United States Patent
Oh et al.

(10) Patent No.: US 12,285,544 B2
(45) Date of Patent: Apr. 29, 2025

(54) CONDUCTIVE GRAPHENE/CARBON NANOFIBER COMPOSITE SCAFFOLD, ITS USE FOR NEURAL TISSUE ENGINEERING AND A METHOD OF PREPARATION THEREOF

(71) Applicant: The Board of Trustees of the Leland Stanford Junior University, Stanford, CA (US)

(72) Inventors: Byeongtaek Oh, Columbia, MD (US); Vivek Nath Lam, Palo Alto, CA (US); Paul George, Sunnyvale, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 531 days.

(21) Appl. No.: 16/647,976

(22) PCT Filed: Oct. 4, 2018

(86) PCT No.: PCT/US2018/054452
§ 371 (c)(1),
(2) Date: Mar. 17, 2020

(87) PCT Pub. No.: WO2019/071033
PCT Pub. Date: Apr. 11, 2019

(65) Prior Publication Data
US 2020/0222591 A1 Jul. 16, 2020

Related U.S. Application Data

(60) Provisional application No. 62/568,765, filed on Oct. 5, 2017.

(51) Int. Cl.
| | | |
|---|---|---|
| A61L 27/44 | (2006.01) | |
| A61L 27/08 | (2006.01) | |
| A61L 27/38 | (2006.01) | |
| A61L 27/52 | (2006.01) | |
| A61L 27/56 | (2006.01) | |
| C08L 101/12 | (2006.01) | |

(52) U.S. Cl.
CPC .............. *A61L 27/44* (2013.01); *A61L 27/08* (2013.01); *A61L 27/3834* (2013.01); *A61L 27/3895* (2013.01); *A61L 27/52* (2013.01); *A61L 27/56* (2013.01); *C08L 101/12* (2013.01); *A61L 2400/12* (2013.01)

(58) Field of Classification Search
None
See application file for complete search history.

(56) References Cited

U.S. PATENT DOCUMENTS

| | | | |
|---|---|---|---|
| 9,555,583 B1 * | 1/2017 | Dirk | B33Y 10/00 |
| 2015/0044259 A1 | 2/2015 | DeSilva | |
| 2015/0141711 A1 | 5/2015 | Chu | |
| 2015/0259212 A1 * | 9/2015 | Li | B82Y 40/00 |
| | | | 428/221 |
| 2017/0130194 A1 | 5/2017 | Lee | |

FOREIGN PATENT DOCUMENTS

| | | | |
|---|---|---|---|
| CN | 102274521 | 3/2013 | |
| WO | WO2015109272 | 7/2015 | |
| WO | WO-2015109272 A1 * | 7/2015 | ............. C01B 31/02 |
| WO | WO2017011452 | 1/2017 | |

OTHER PUBLICATIONS

Sui, Z., et al., Green synthesis of carbon nanotube-graphene hybrid aerogels and their use as versatile agents for water purification, Carbon 49(7) 4314-4321 (2011); see IDS filed Mar. 17, 2020.*
Sui, Z., et al., Green synthesis of carbon nanotube-graphene hybrid aerogels and their use as versatile agents for water purification, J. Mater. Chem., 2012, 22, 8767-71 (Year: 2012).*
Sui, Z., et al., Green synthesis of carbon nanotube-graphene hybrid aerogels and their use as versatile agents for water purification, J. Mater. Chem., 2012 Supplemental Information (Year: 2012).*
Sui, Z., Zhang, X., et al., Easy and green synthesis of reduced graphite oxide-based hydrogels, Carbon 49 (2011) 4314-21 (Year: 2011).*
Carbon nanofiber (https://en.wikipedia.org/wiki/Carbon_nanofiber, accessed Nov. 4, 2022 (Year: 2022).*
Kostarelos, K., et al., Graphene in the Design and Engineering of Next-Generation Neural Interfaces, Adv. Mater. 2017, 29, 1700909 (Year: 2017).*
Sui et al. Easy and green systhesis of reduced graphite oxide-based hydrogels. Carbon 49(7) 2011 4314-4321, Pub'd 2011.
Sui et al. Green systhesis of carbon nanotube-graphene aerogels and their use as versatile agents for water purification. J. Material Chemistry 22(30) 2012 8767-8771.
Carbon Nanofiber Wikipedia Sep. 8, 2017.

* cited by examiner

*Primary Examiner* — H. Sarah Park
(74) *Attorney, Agent, or Firm* — LUMEN PATENT FIRM (57) ABSTRACT

Porous electrically conductive graphene/carbon nanofiber bio-scaffolds can be fabricated having a Youngs modulus and electrical conductivity that both match typical values for brain tissue. Such scaffolds have been tested and found to provide improved differentiation of stem cells into functional neural cells relative to conventional scaffolds. In preferred embodiments, neural cell differentiation in conductive graphene/carbon nanofiber scaffolds is promoted by an applied electrical stimulus.

6 Claims, 7 Drawing Sheets

CONDUCTIVE GRAPHENE/CARBON NANOFIBER COMPOSITE SCAFFOLD, ITS USE FOR NEURAL TISSUE ENGINEERING AND A METHOD OF PREPARATION THEREOF

FIELD OF THE INVENTION

This invention relates to biological scaffolds, especially for cell growth and differentiation.

BACKGROUND

The development of new conductive bio-scaffolds has acquired a great deal of importance in biomedical engineering. The main requirement is to design a scaffold that mimics the relevant biological and mechanical properties of human tissues. However, conventional work in the field has not yet demonstrated conclusively which of the various possible parameters are most relevant for this application.

Such scaffolds are of particular interest for neural tissue engineering. Work to date on these scaffolds has limited success in terms of differentiation of stem cells into functional neural cells. Accordingly, it would be an advance in the art to provide improved bio-scaffolds, especially for neural tissue engineering.

SUMMARY

We have found that porous conductive graphene/carbon nanofiber scaffolds can be fabricated having a Young's modulus and electrical conductivity that both match typical values for brain tissue. Furthermore, such scaffolds have been tested and found to provide improved differentiation of stem cells into functional neural cells relative to conventional scaffolds. In preferred embodiments, neural cell differentiation in conductive graphene/carbon nanofiber scaffolds can be promoted by an applied electrical stimulus and/or by the mechanical stimulus inherently provided by the scaffold.

More specifically, the present disclosure is directed to developing a conductive polymer scaffold with soft mechanical characteristics, which can be fabricated with a varying ratio of carbon nanofibers. Electrical signals between cells and surrounding tissues modifies neural activity and stem cell reorganization, migration, proliferation, and differentiation. The properties of the scaffold which is electrically conductive and 3D macro-porous while being mechanically soft creates the ability to manipulate the stem cells more effectively.

In one general aspect, the present disclosure provides a method for fabricating a soft conductive graphene scaffold (soft-CGS) having reduced graphene oxide/carbon nanofibers including steps of: 1) preparing graphene oxide (GO) suspension in presence of carbon nanofiber (CNF); 2) sonicating the solution until it showed homogenous dispersion of graphene oxide/carbon nanofiber mixture; and 3) reducing the graphene oxide using reducing agents.

Our new method allows for altering the stiffness of the CGS by controlling the ratio of CNF to GO. The soft-CGS is electrically conductive and mechanically soft. The conductivity does not seem to be altered by changing the ratio of CNFs. In one example, the sol-gel process creates a porous scaffold with pores ranging from 15-70 µm with an average pore size of 31.3 µm. In addition, morphological characterization by SEM indicates that the CGS have three dimensional structures and pores. Subsequent FT-IR and XPS analyses demonstrate that graphene oxide intertwined with carbon nanofibers was fully reduced, resulting from a sol-gel transition of the solution. FT-IR analysis shows that the fully reduced GO structure has negligible oxide groups. XPS analysis demonstrates that the CGS structure has minimal C—O and O—C=O bands. Additionally, the CGS structure has a high $SP^2$ carbon band peak indicating a gelled CGS.

This work has various applications. The improved properties of the graphene/carbon nanofiber based conductive scaffolds of this work expand their utility compared to conventional graphene-based materials that are typically brittle. For example, these graphene/carbon nanofiber foams may find application in electrodes for energy storage, and in conversion devices such as supercapacitors, fuel cells and batteries, in capacitive desalination devices, in thermal and acoustic insulators, in chemical or mechanical sensors, in biomedical applications, in actuators, in adsorbents, as catalyst supports, in field emission, as a precursor for graphene-based film processing, in mechanical dampening, as filters, and in three dimensional flexible electronic components. These graphene/carbon nanofiber conductive scaffolds can also be utilized in biomedical applications, since the scaffold is biocompatible. The highly porous micro-niche and elastic modulus in the presence of carbon nanofibers provides a soft scaffold for tissue engineering. Moreover, the high electrical conductivity allows the use of electrical stimulation for controlling the differentiation and paracrine release of stem cells, maximizing the utilization of stem cells for tissue engineering including neural recovery applications.

Significant advantages are provided. Because stem cells target brain repair and thus can have a therapeutic effect months or even years post-injury, their use as treatment options for various brain diseases including stroke, Alzheimer's disease and glioblastoma has the potential to impact the vast majority of survivors. However, ineffective delivery of transplanted cells to the ischemic site is a major hurdle, hampering the clinical application of human induced pluripotent stem cells (hiPSCs)-based stroke therapy. One of the main challenges in stem cell transplantation is to minimize cell death after implantation and maintain electrical interactions with the cells after seeding. With the use of a conductive scaffold to provide an appropriate stem cell niche, the human induced pluripotent stem cells can be transplanted into the human brain to restore function shortly after a stroke. The improved properties of the graphene/carbon nanofiber conductive scaffolds of this work provide an implantable, porous, and conductive graphene scaffold to create a new paradigm to augment stem cell-induced brain disease treatments as well as introduce a new method of stem cell delivery.

DETAILED DESCRIPTION

Introduction:

To resolve the above-described problem, electrically conductive scaffolds based on graphene oxide and carbon nanofiber (CNF) were prepared by a sol-gel transition associated with a chemical reduction method. Mechanical properties including its modulus have been controlled due to the presence of carbon nanofibers. The addition of carbon nanofibers created a soft conductive scaffold which fully mimics the microenvironment of brain tissue. This work provides a conductive bio-scaffold which overcomes the drawbacks of conventional inert scaffolds in neural tissue engineering.

Figure 1A:
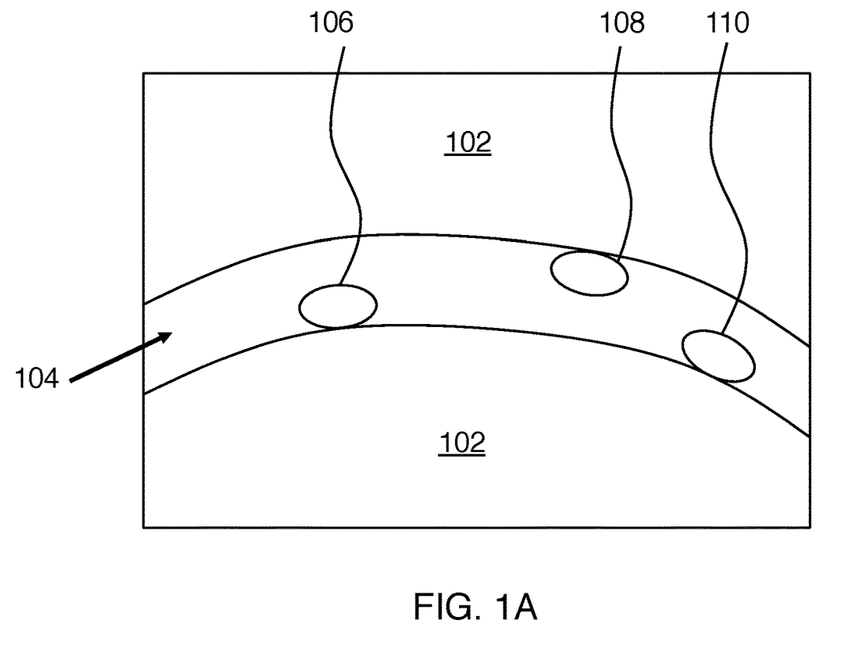
FIGS. 1A-B schematically show use of a bio-scaffold to expedite differentiation of stem cells into neural cells.
Figure 1B:
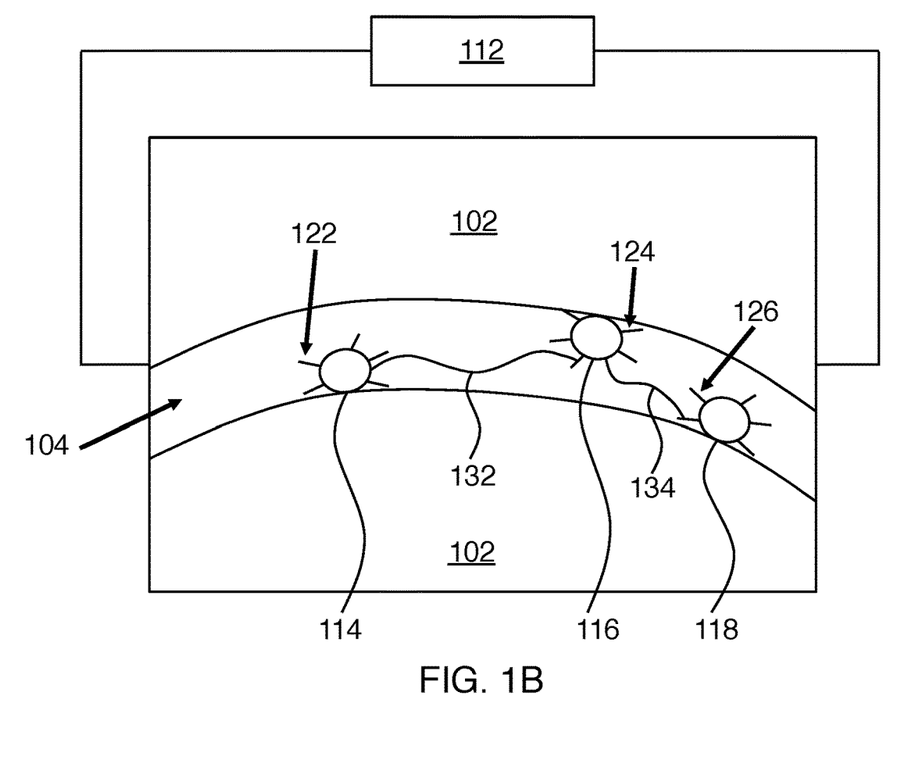

FIGS. 1A-B schematically show use of a bio-scaffold to expedite differentiation of stem cells into neural cells. FIG. 1A schematically shows stem cells 106, 108, 110 infiltrated into a pore 104 in a scaffold 102. The desired result of this is shown on FIG. 1B, where the stem cells have differentiated into neural cells 114, 116, 118 having functional structures such as dendrites 122, 124, 126 and axons 132 and 134. Preferably, as shown, axons and dendrites are functionally connected from one neural cell to another. Stimulation 112 can be applied to facilitate this process of differentiation. In general, the success or failure of this kind of approach will depend critically on the properties of the scaffold, and in particular on how well the relevant properties of brain tissue are reproduced by the scaffold. As indicated above, we have found that providing a close match for both mechanical stiffness (i.e., Young's modulus) and electrical conductivity leads to improved neural cell differentiation compared to conventional scaffold materials.

One embodiment of the invention is a method of making an electrically conductive graphene/carbon nanofiber composite scaffold. The method includes the following steps:
1) preparing a suspension of graphene oxide and carbon nanofibers;
2) sonicating the suspension to ensure a homogeneous mixture of the graphene oxide and carbon nanofibers; and
3) reducing the graphene oxide in the suspension with one or more reducing agents to provide an electrically conductive graphene/carbon nanofiber composite scaffold via a sol-gel transition. A detailed example is described below in the methods section.

Some general features of preferred embodiments are described here. These features can be included in the above method individually or in any combination. The graphene oxide can be prepared by reacting graphite with an oxidizer in an acidic solution. The suspension can be degassed after the sonicating of step 2 and prior to the reducing of step 3. Pores of the scaffold can have pore diameters in a range from 15 μm to 70 μm. The Young's modulus of the scaffold is preferably between 3 kPa and 7 kPa. The electrical conductivity of the scaffold is preferably between 0.1 S/m and 0.3 S/m. The X-ray photoelectron spectrum of the scaffold preferably has an $SP^1$ C peak that is larger than its C—O peak. This result is a signature of full reduction of graphene oxide to graphene in the sample.

Another embodiment of the invention is a method of directing stem cell differentiation. Here the steps include providing a scaffold made as described above, and exposing the scaffold to a culture medium comprising stem cells for a period of time sufficient to allow the stem cells to differentiate into cells of interest. The differentiation of the stem cells into cells of interest in the culture medium can be driven by one or more external stimulations (e.g., 112 on FIG. 1B). The external stimulations are preferably electrical stimulation.

A further embodiment of the invention is an electrically conductive graphene/carbon nanofiber composite scaffold, where the electrically conductive graphene/carbon nanofiber composite scaffold is porous with a 3-D network of pores. Here composite refers to the carbon nanofibers being physically incorporated into the scaffold without being chemically bonded to the graphene.

Some general features of preferred embodiments are described here. These features can be included in the above scaffold individually or in any combination. Pores of the scaffold can have pore diameters in a range from 15 μm to 70 μm. The Young's modulus of the scaffold is preferably between 3 kPa and 7 kPa. The electrical conductivity of the scaffold is preferably between 0.1 S/m and 0.3 S/m. The X-ray photoelectron spectrum of the scaffold preferably has an $SP^2$ C peak that is larger than its C—O peak. This result is a signature of full reduction of graphene oxide to graphene in the sample. Differentiated stem cells can be disposed in the scaffold.

Figure 2A:
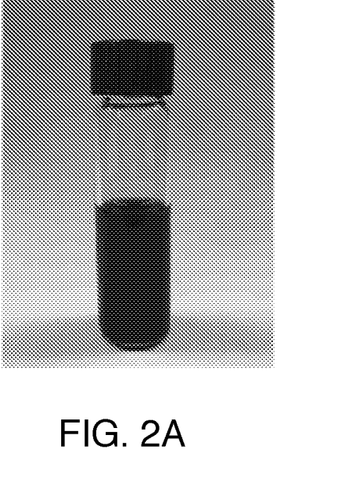
FIGS. 2A-B are images showing two stages of an exemplary fabrication sequence for conductive graphene/carbon nanofiber scaffolds.
Figure 2B:
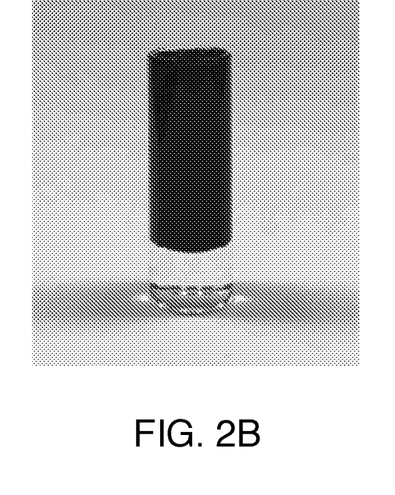

Experimental Example:

FIGS. 2A-B are photographs of conductive graphene scaffold (CGS) before chemical reduction (Sol-status, (FIG. 2A)) and after chemical reduction (Gel-status, (FIG. 2B)).

Figure 3A:
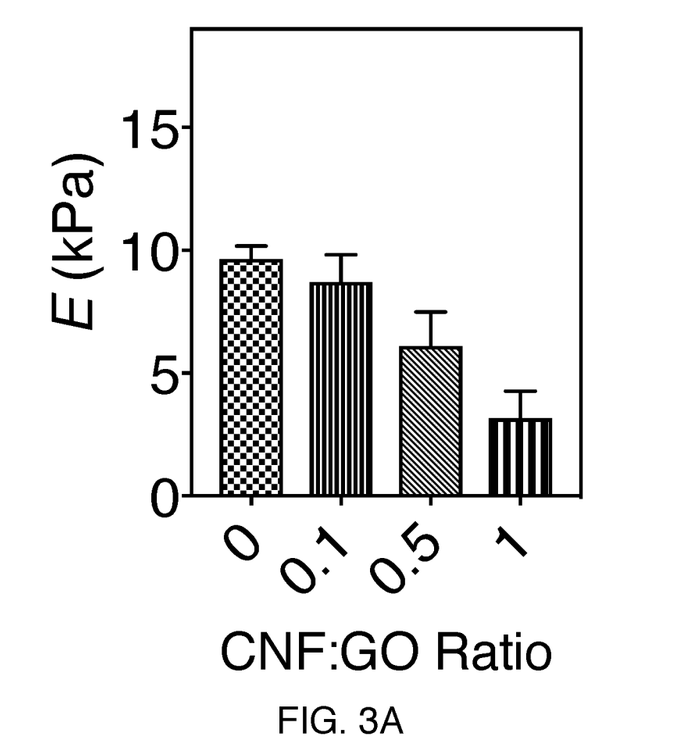
FIG. 3A shows stiffness of conductive graphene/carbon nanofiber scaffolds vs. ratio of carbon nanofibers to graphene oxide.

FIG. 3A shows how addition of different ratio of carbon nanofibers can modulate its stiffness. FIG. 3A is a bar graph showing Young's modulus (ranging from ~12 kPa (No addition of carbon nanofibers, Stiff-CGS) to ~3 kPa (GO: CNFs, 1:1, Soft-CGS)) with different ratio of carbon nanofibers in the scaffolds. Data are presented as mean±standard deviation.

Figure 3B:
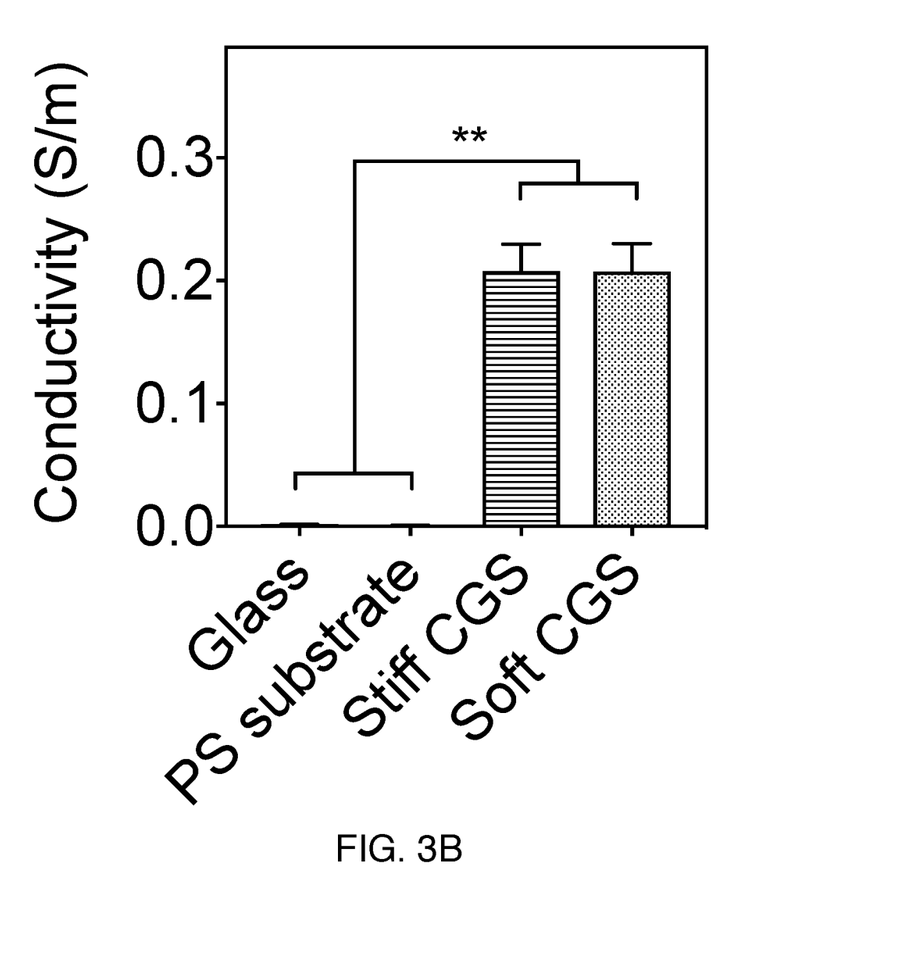
FIG. 3B shows electrical conductivity of conductive graphene/carbon nanofiber scaffolds compared to that of other scaffold materials.

FIG. 3B shows electrical conductivity of scaffolds of this work as compared to the electrical conductivity of other scaffold materials. The conductivity and elastic modulus can mimic physiological brain, which we have found to provide rapid neuronal conversion of stem cells into functional neurons.

Figure 4A:
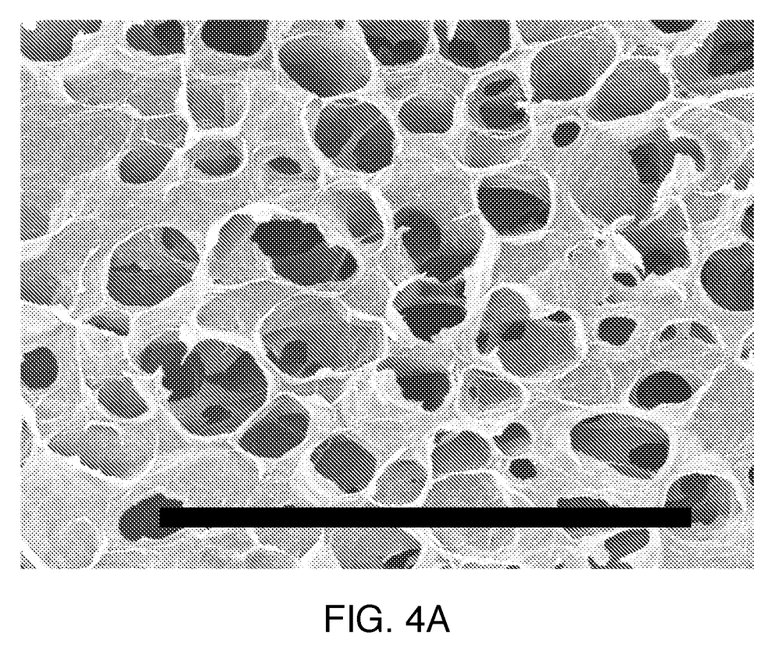
FIGS. 4A-C are SEM (scanning electron microscope) images from a fabricated conductive graphene/carbon nanofiber scaffold.

FIG. 4A is an image of surface morphology of a fabricated conductive graphene scaffold showing its porous structure. The scale bar indicates 200 μm.

Figure 4B:
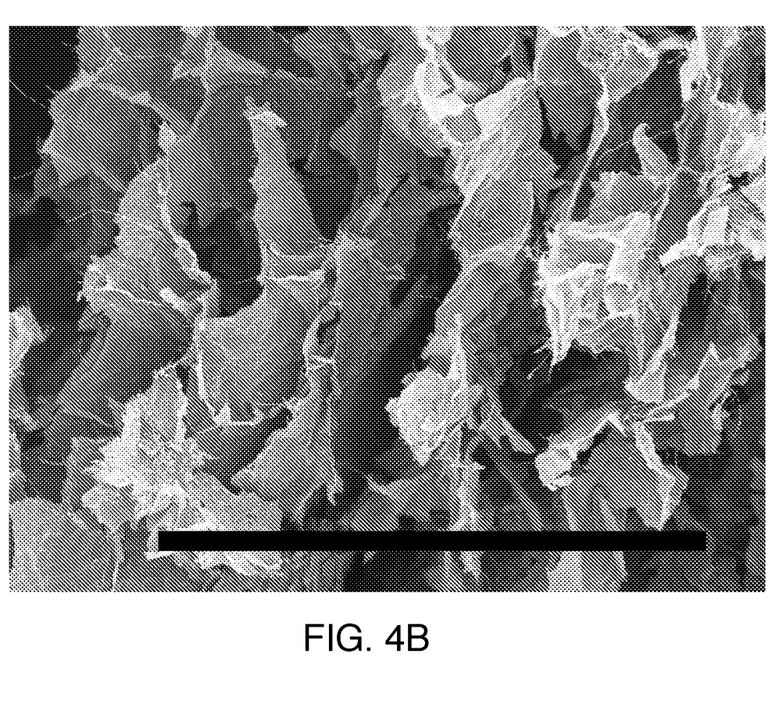

FIG. 4B is a cross sectional image showing the porous structure inside the conductive graphene scaffold. The scale bar indicates 200 μm.

Figure 4C:
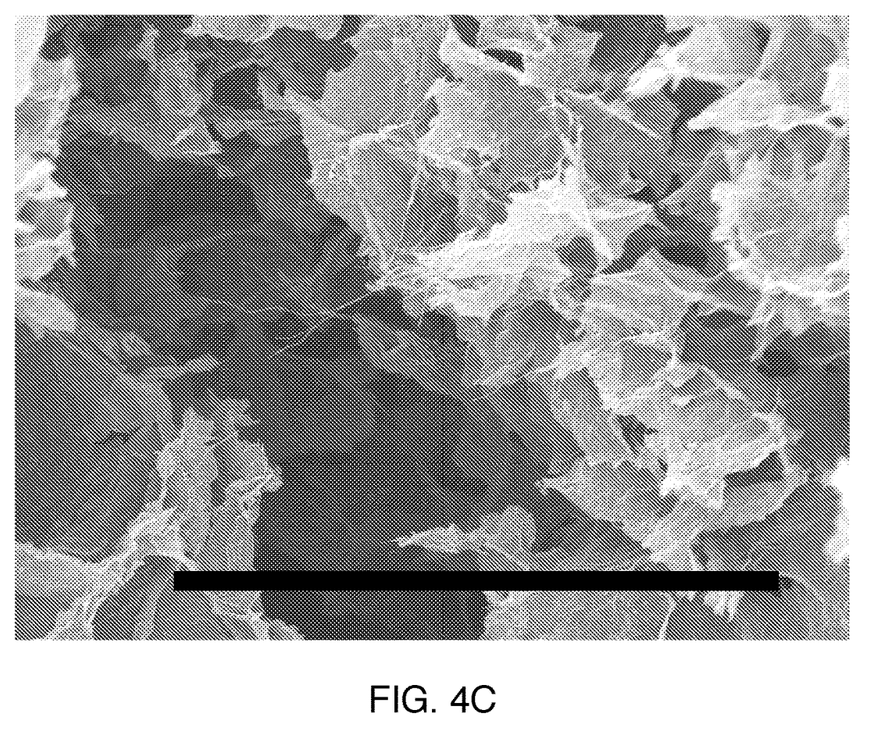

FIG. 4C is an image of carbon nanofibers intertwined with reduced graphene oxides (rGOs) inside the conductive graphene scaffold. The scale bar indicates 400 μm.

Figure 5:
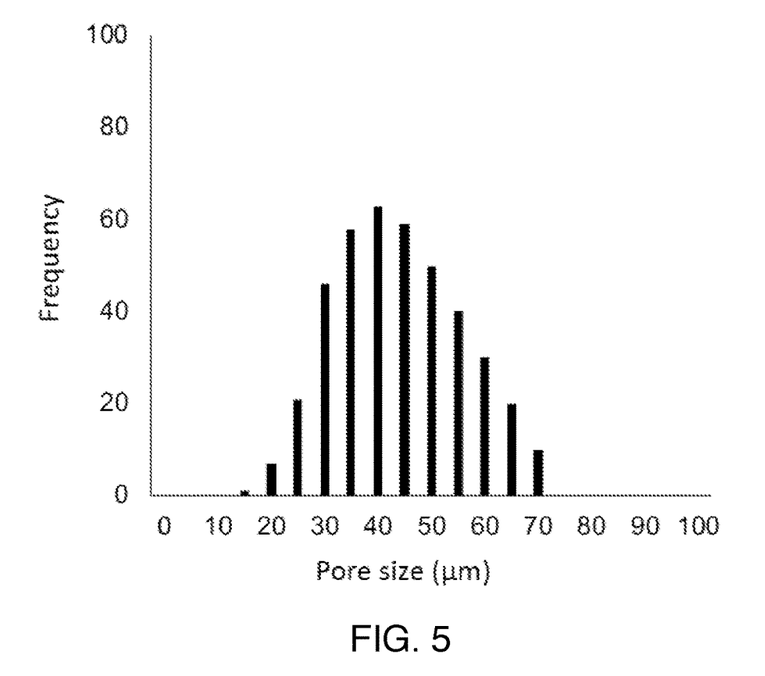
FIG. 5 is a histogram of the pore size from a sample of a conductive graphene/carbon nanofiber scaffold.

FIG. 5 is a histogram of pore size distribution in a fabricated conductive graphene scaffold. The average pore size in this sample was 31.3 μm and the standard deviation was 2.3 μm. Here pore size is the pore diameter, as opposed to the pore radius.

Figure 6:
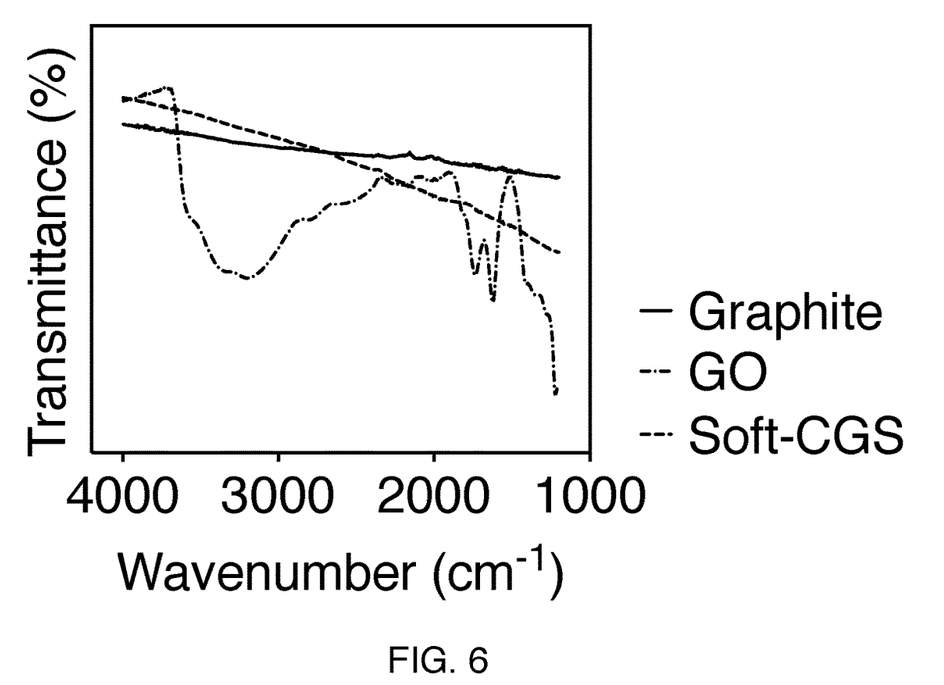
FIG. 6 shows FTIR (Fourier Transform InfraRed) spectra from graphite, graphene oxide and a fabricated conductive graphene/carbon nanofiber scaffold.

FIG. 6 shows FT-IR (Fourier Transform InfraRed spectroscopy) analysis of different materials. GO (graphene oxide) was fully reduced by reducing agents, forming the conductive graphene scaffold. In presence of carbon nanofibers, the soft conductive graphene scaffold sample (Soft-CGS) showed negligible oxide groups, such as —OH (~3200 cm-1) and —COOH (~1700 cm-1). These results indicate that the fabrication of the conductive graphene scaffold was achieved by chemical reduction which induced a sol-gel transition of the solution.

Figure 7A:
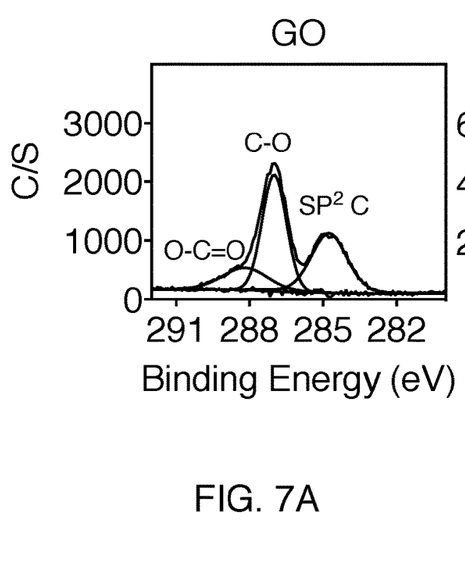
FIG. 7A shows XPS (X-ray photoelectron Spectroscopy) data from a graphene oxide sample.
Figure 7B:
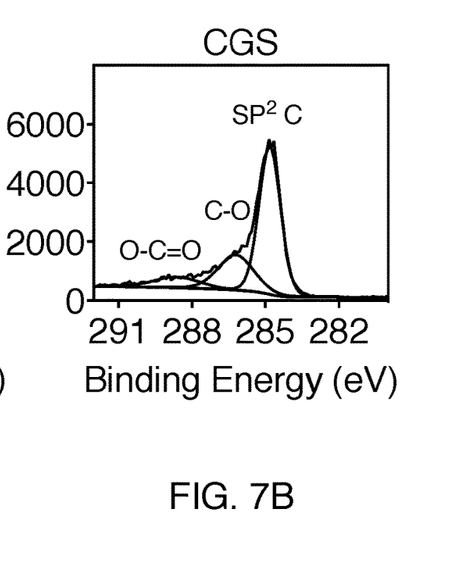
FIG. 7B shows XPS data from a fabricated conductive graphene/carbon nanofiber scaffold sample.

FIGS. 7A-B show results of XPS (X-ray Photoelectron Spectroscopy) analysis probing the mechanism of gelation during conductive graphene scaffold synthesis, where graphene oxide was reduced in presence of reducing agents. FIG. 7A shows the graphene oxide XPS results, which include peaks from oxide groups such as C—O and O—C=O as labeled on the plot. FIG. 7B shows the conductive graphene scaffold XPS results. Here the conductive graphene scaffold didn't have high C—O and O—C=O bands. Exceptionally, the conductive graphene scaffold showed high peak of SP2 carbon band, indicating that while reducing oxides, reduced graphene oxides were intertwined with carbon nanofibers due to hydrophobic interaction, eventually forming a gelled conductive graphene scaffold.

Figure 8A:
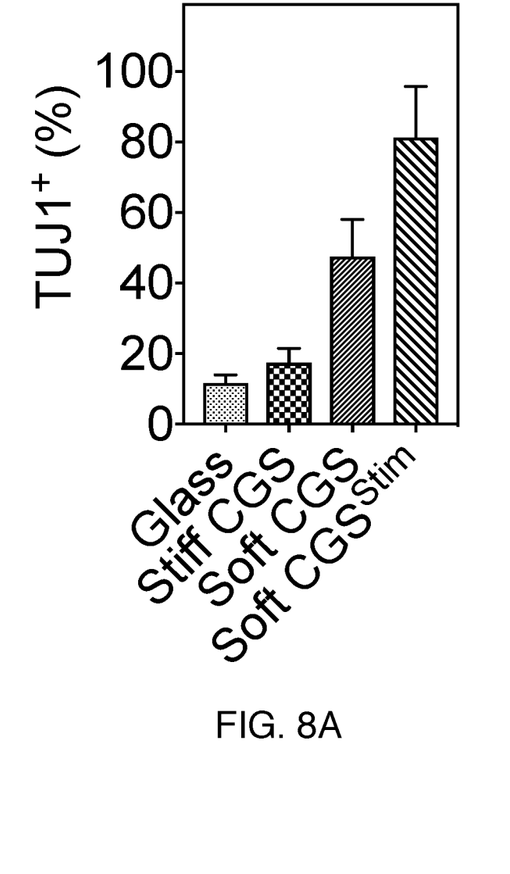
FIGS. 8A-B show neural cell differentiation results for various scaffold materials and conditions.
Figure 8B:
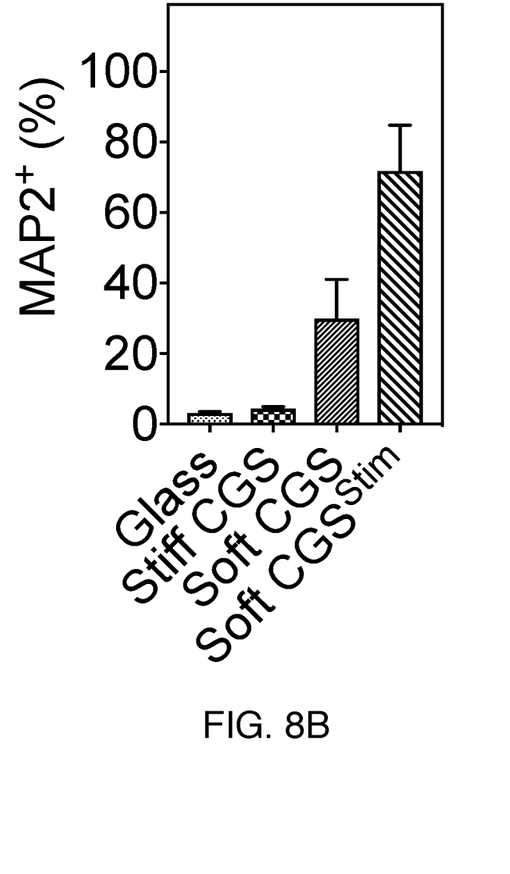

FIGS. 8A-B are bar plots showing the proportion of TUJ1$^+$ (FIG. 8A) and MAP2$^+$ (FIG. 8B) cells (neuronal markers) differentiated from human-induced pluripotent stem cells at 14 days with conditions as described below in the methods section. Here TUJ1 is short for 'Neuron-specific Class III beta-tubulin' and MAP2 is short for 'Microtubule associated protein-2'. The soft conductive graphene scaffold that was electrically stimulated showed more rapid maturation of stem cells into neurons than other conditions as well as more rapid maturation than has been reported in the literature using chemical factors. Note that TUJ1 is an earlier marker of neurons, but MAP2 is post-mitotic stage marker of neurons. Thus, cells could have TUJ1+ cells with smaller population of MAP2+ cells. In other words, the markers are not exclusive so cells can show both markers, but the ones with MAP2 are more mature.

Methods:
1) Preparation of graphene oxides (GOs): 1 g of graphite flakes (Ashbury Carbon, NJ) supplied from Ashbury Carbons (Asbury, NJ) was added into acidic solution (9:1, $H_2SO_4$:$HNO_3$) and the solution was stirred without heat for 30 min. 6 g of potassium permanganate was slowly added into the solution, and the solution was covered with tin foil, heat to 50° C., and incubate overnight. 5 mL of $H_2O_2$ ice-cold solution was added and stirred for 2 hours until no bubbles found. The solution was centrifuged at 4,500 rpm for 45 min. The purification with HCl (0.1 M) and three consecutive washing with DI $H_2O$ was applied to remove unreacted carbon and metal ions. Collected graphene oxides (10 mg/ml) was kept at 4° C. until further usage.
2) Preparation of 3D-nanoconfined conductive graphene scaffold (3D CGS): Carbon nanofibers were purchased from Sigma Aldrich, and had diameter ~100 nm and length ~20-200 μm (manufacturer's specifications). Equal amount of carbon nanofibers were suspended in graphene oxide solution to a concentration of 0.2 wt %. Suspensions were sonicated using a bath sonicator (Branson Ultrasonic) for 1 hour at 60 W followed by centrifugation at 2,000 rpm for 20 min (Beckman Coulter Allegra 25R) to sediment carbon nanofiber bundles. We degassed the concentrated GO:CNF suspensions to remove any bubbles since bubbles significantly degrade the mechanical integrity of 3D CGS. Reducing agents including sodium iodide and ascorbic acid to a concentration of 10 wt % to induce self-assembly of 3D CGS were added into suspensions and it was poured into cylindrical molds. The suspensions formed 3D CGS via solution to gelation transition (sol-gel transition) at 80° C. within 24 hours due to van der Walls interactions between reduced-GOs/CNFs in presence of reducing agents. 3D CGS had dimensions of 6×2 mm (diameter×height). The 3D CGSs were neutralized by washing with deionized water until pH equilibrated to 7. Collected 3D CGSs were autoclaved and was kept at 4° C. until further usage.
3) Differentiation of neural progenitor cells (NPCs) to neurons using electrical stimulation: NPCs were plated on CGS (100,000 cells/cm$^2$) previously coated with 10 μg/ml poly-L-ornithine solution (Sigma-Aldrich, St. Louis, MO) and 4 μg/ml laminin (Sigma-Aldrich, St. Louis, MO) in PBS (phosphate-buffered saline). Then scaffolds with the cells were incubated under standard cell culture conditions (37° C., 5% $CO_2$) for 24 hr. In vitro iPSC-electrical stimulation was applied by means of an alternating current-electrical stimulation. Here iPSC is short for 'induced pluripotent stem cells'. The chamber includes parallel ITO (indium tin oxide) patterned-electrodes, separated by a distance of 3 mm. The electrodes were connected to a waveform generator (Keysight, Englewood, CO). The cells cultured on CGS were exposed to electrical stimulation for 1 hr. After the stimulation was applied, the scaffolds were carefully transferred to a 24-well plate with 1 mL of fresh medium. On day 7, cells were fixed with 4% paraformaldehyde (Electron Microscopy Sciences) for 1 min and then permeabilized and blocked with blocking buffer (0.1% Triton X-100, 1% BSA (Fisher BioReagents, Santa Clara, CA), 5% normal goat serum (NGS, Invitrogen, Waltham, MA) for 1 hr at room temperature. Primary antibodies (TUJ1 And MAP2) were incubated in blocking buffer at 4° C. overnight, followed by three 15-min PBS washes and detected by secondary antibodies (Alexa Flour 488, 555 or 647, Life Technologies). Samples were counter-stained with DAPI (Sigma-Aldrich, St. Louis, MO) to visualize nuclei and mounted with Fluoromount Aqueous Medium (Sigma-Aldrich, St. Louis, MO) before imaging. Samples were imaged on a Keyence All-in-One Fluorescence Microscope (BZ-X700) (Keyence corp., Itasca, IL) using 20× objectives. Image of cells on CGSs are presented as maximum intensity projections of z-stacks generated from BZ-X Analyzer. The neuronal differentiation efficacy of iPSCs was quantified by counting the total number of TUJ1-positive cells with neuronal morphology. The number of TUJ1-positive cells was divided by the total number of cell nuclei (DAPI-positive) to demonstrate the percentage of neuronal differentiation. Calculations were performed using randomly selected 4 different locations from 4 individual samples at 20× magnification.

The invention claimed is:
1. A method of making an electrically conductive graphene/carbon nanofiber composite scaffold, the method comprising:
preparing a suspension of graphene oxide and carbon nanofibers;
sonicating the suspension to ensure a homogeneous mixture of the graphene oxide and carbon nanofibers;

reducing the graphene oxide in the suspension with one or more reducing agents to provide an electrically conductive graphene/carbon nanofiber composite scaffold via a sol-gel transition; and degassing the suspension after the sonicating and prior to the reducing;

wherein a ratio of carbon nanofibers to graphene oxide is selected to provide a Young's modulus of the scaffold that is between 3 kPa and 7 kPa;

wherein an electrical conductivity of the scaffold is between 0.1 S/m and 0.3 S/m.

2. The method of claim 1, wherein the graphene oxide is prepared by reacting graphite with an oxidizer in an acidic solution.

3. The method of claim 1, wherein pores of the scaffold have pore diameters in a range from 15 μm to 70 μm.

4. A method of directing stem cell differentiation, the method comprising:

providing a scaffold made according to the method of claim 1; and exposing the scaffold to a culture medium comprising stem cells for a period of time sufficient to allow the stem cells to differentiate into cells of interest.

5. The method of claim 4, wherein differentiation of the stem cells into cells of interest in the culture medium is driven by an external electrical stimulation.

6. The method of claim 1, wherein an X-ray photoelectron spectrum of the scaffold has an $SP^2$ C peak that is larger than its C—O peak.

* * * * *

UNITED STATES PATENT AND TRADEMARK OFFICE
CERTIFICATE OF CORRECTION

| | |
|---|---|
| PATENT NO. | : 12,285,544 B2 |
| APPLICATION NO. | : 16/647976 |
| DATED | : April 29, 2025 |
| INVENTOR(S) | : Byeongtaek Oh et al. |

Page 1 of 1

It is certified that error appears in the above-identified patent and that said Letters Patent is hereby corrected as shown below:

In the Specification

Column 1, Line 11, add the following statement:
STATEMENT OF GOVERNMENT SUPPORT
This invention was made with Government support under contract NS089976 awarded by the National Institutes of Health. The Government has certain rights in the invention.

Signed and Sealed this
Twenty-third Day of September, 2025

John A. Squires
*Director of the United States Patent and Trademark Office*